United States Patent [19]

Bergstrom et al.

[11] Patent Number: 5,102,907
[45] Date of Patent: Apr. 7, 1992

[54] NOVEL SQUALENE SYNTHETASE INHIBITORS

[75] Inventors: James D. Bergstrom, Neshanic; Claude Dufresne, Edison; Leeyuan Huang, Watchung; Mary Nallin, Westfield; Janet C. Onishi, Mountainside, all of N.J.

[73] Assignee: Merck & Co., Inc., Rahway, N.J.

[21] Appl. No.: 582,452

[22] Filed: Sep. 13, 1990

[51] Int. Cl.$^5$ ................ C07D 319/14; A61K 31/35
[52] U.S. Cl. .................................... 514/456; 549/363
[58] Field of Search ...................... 549/363; 514/456

[56] References Cited

U.S. PATENT DOCUMENTS 4,871,721 10/1989 Biller .................................. 514/102

FOREIGN PATENT DOCUMENTS 045631 7/1980 European Pat. Off. ............ 549/363

OTHER PUBLICATIONS

S. A. Biller et al., *J.Med.Chem.*, 31, 1869 (1988).
C. D. Poulter et al., *J. Am. Chem. Soc.*, 111, 3734 (1989).
E. J. Corey et al., *J. Am. Chem. Soc.*, 98, 1291 (1976).

*Primary Examiner*—C. Warren Ivy
*Assistant Examiner*—Celia Chang
*Attorney, Agent, or Firm*—Joseph F. DiPrima; Melvin Winokur

[57] ABSTRACT

This invention relates to compounds of structural formula (I):

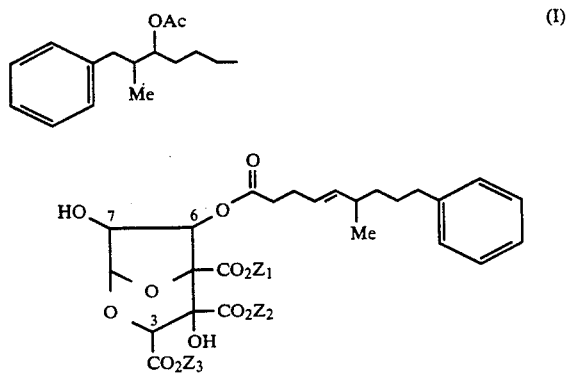

which are squalene synthetase inhibitors and thus useful as cholesterol lowering agents.

12 Claims, No Drawings

NOVEL SQUALENE SYNTHETASE INHIBITORS

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e. several grams at a time and they are not very palatable.

MEVACOR® (lovastatin), now commercially available, is one of a group of very active antihypercholesterolemic agents that function by limiting cholesterol biosynthesis by inhibiting the enzyme, HMG-CoA reductase.

Squalene synthetase is the enzyme involved in the first committed step of the de novo cholesterol biosynthetic pathway. This enzyme catalyzes the reductive dimerization of two molecules of farnesyl pyrophosphate to form squalene. The inhibition of this committed step to cholesterol should leave unhindered biosynthetic pathways to ubiquinone, dolichol and isopentenyl t-RNA.

Previous efforts at inhibiting squalene synthetase have employed pyrophosphate or pyrophosphate analog containing compounds such as those described in P. Ortiz de Montellano et al, J. Med Chem. 20, 243 (1977) and E. J. Corey and R. Volante, J. Am. Chem. Soc., 98, 1291 (1976). S. Biller (U.S. Pat. No. 4,871,721) describes isoprenoid (phosphinylmethyl)phosphonates as inhibitors of squalene synthetase.

The present invention provides nonphosphorus containing inhibitors of squalene synthetase.

DETAILED DESCRIPTION OF THE INVENTION

The present invention is directed to novel compounds of structural formula (I) which are squalene synthetase inhibitors:

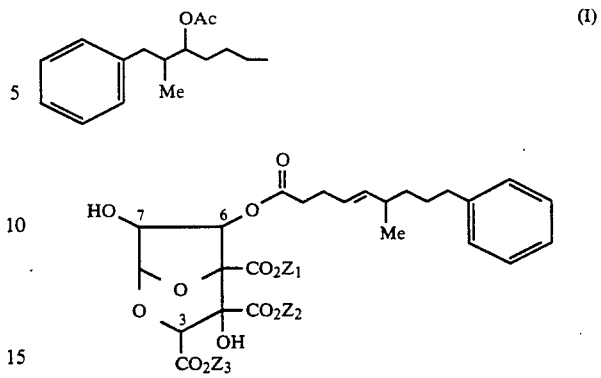

wherein $Z_1$, $Z_2$ and $Z_3$ are each independently selected from;
a) H;
b) $C_{1-5}$alkyl;
c) $C_{1-5}$alkyl substituted with a member of the group consisting of:
  i) phenyl,
  ii) phenyl substituted with methyl, methoxy, halogen (Cl, Br, F, I) or hydroxy; or a pharmaceutically acceptable salt of a compound of of formula (I).

In one embodiment of the present invention are those compounds of formula (I) wherein the relative stereochemical configuration of the 2,8-dioxabicyclo[3.2.1]octane ring is as shown below:

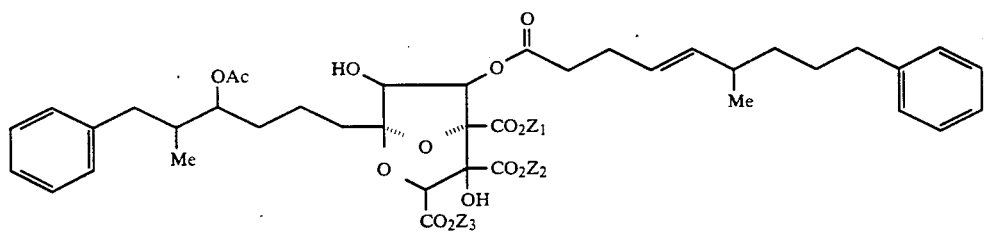

Throughout this specification and claims where stereochemistry is described for the dioxabicyclo[3.2.1]octane ring the configuration implied is relative. The actual configuration may be shown or that of its enantiomer.

Further illustrating this embodiment are those compounds of structural formula (I) wherein the relative configuration at positions 3, 6 and 7 is as shown below:

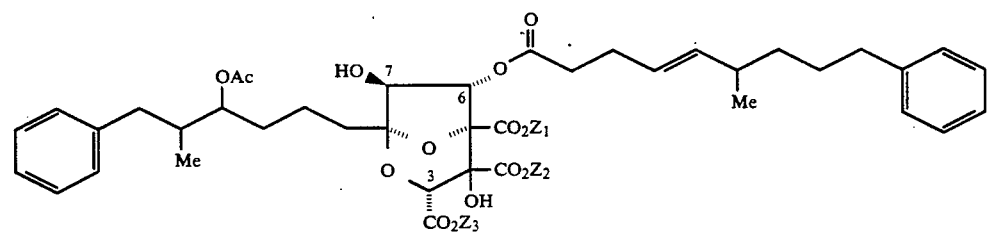

In one class of this embodiment are those compounds of structure (I) wherein the relative configuration at the 4-position is as shown below:

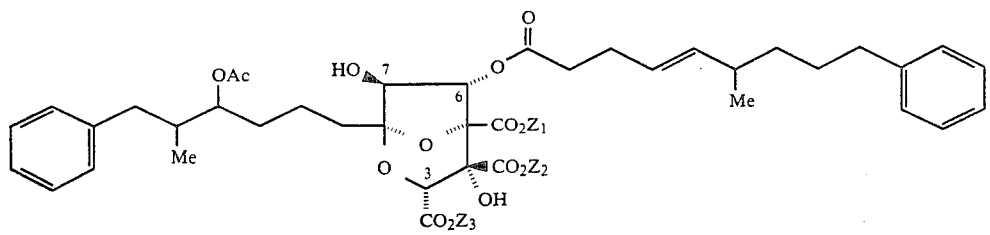

Exemplifying this class is the compound wherein $Z_1$, $Z_2$ and $Z_3$ are each hydrogen or a pharmaceutically acceptable salt thereof. The compound wherein $Z_1$, $Z_2$ and $Z_3$ are each hydrogen is hereafter referred to as Compound A.

Further illustrating this class are those compounds in which one or more of $Z_1$, $Z_2$ or $Z_3$ is $C_{1-5}$alkyl or $C_{1-5}$alkyl substituted with phenyl or substituted phenyl wherein the substituent is methyl, methoxy, halogen or hydroxy. In a specific illustration, $Z_1$, $Z_2$ and $Z_3$ are each methyl. This compound is hereafter referred to as Compound B.

The compounds of formula (I) are prepared in an aerobic fermentation procedure employing a novel fungal culture, MF5465, identified as *Leptodontium elatius*. Although the use of this organism is specifically described herein, other species of the genus Leptodontium including mutants of the above described organism are also capable of producing compounds of this invention.

The culture MF5465 is that of a fungus, a lignicolous Hyphomycete, *Leptodontium elatius*, isolated from wood in the Joyce Kilmer Memorial Forest in North Carolina. This culture has been deposited with the American Type Culture Collection at 12301 Parklawn Drive, Rockville, MD 20852 as ATCC 74011.

The culture MF5465, identified as *Leptodontium elatius* exhibits the following morphological features.

Colonies attaining 12-15 mm in 7 days on oatmeal agar (Difco), with both aerial and submerged mycelium. Colony surface flat to appressed in side view, minutely velvety with a metallic sheen towards the margins, dull towards the center, hyaline at the margin, but soon becoming pale to dark gray, finally black, often developing olivaceous colors in age, Pallid Neutral Gray, Light Gull Gray, Deep Gull Gray, Dark Gull Gray, Slate-Gray, Deep Olive-Gray, Olive-Gray, (capitalized color names from Ridgway, R. 1912. Color Standards and Nomenclature, Washington, D.C.), with similar reverse pigmentation, without exudates diffusible pigments or odors.

Conidiogenous cells holoblastic, arising as the terminal cells of relatively undifferentiated conidiophores, with tapered, subulate apices, with the conidiogenous loci confined to the extreme apex. Occasionally with undifferentiated conidiogenous loci directly on vegetative hyphae. Developing conidia adhere to conidiophore terminus in a thin, irregular to ladder-like rachis in groups of up to 4-15 conidia. Conidiophores originating as undifferentiated branches at right or subacute angles from vegetative hyphae, gradually elongating, remaining simple or forming 1-3-branch points, usually at right to subacute angles, usually clustered in small groups when viewed from above, 1-3 septate, cylindrical to conical with tapered apices hyaline when young but developing olivaceous to olivaceous gray pigments from the base upward in age, with walls slightly thicker than those of vegetative hyphae, 20-65×3-5 μm. Conidia formed abundantly on common media such as oatmeal, malt extract, or corn meal agar, 3.5-5 μm × 1-2 μm, aseptate, smooth, thin-walled, allantoid, suballantoid, to short cylindrical, or narrowly elliptical, often with a small proximal scar or apiculus, without visible slime or gelatinous materials. Hyphae septate, branched, cylindrical or occasionally inflated, up to 5 μm in diameter.

Compounds of this invention can be obtained by culturing the above noted microorganism in an aqueous nutrient medium containing sources of assimilable carbon and nitrogen, preferably under aerobic conditions. Nutrient media may also contain mineral salts and defoaming agents.

The preferred sources of carbon in the nutrient medium are carbohydrates such as glucose, glycerin, starch, dextrin, and the like. Other sources which may be included are maltose, mannose, sucrose, and the like. In addition, complex nutrient sources such as oat flour, corn meal, millet, corn and the like may supply utilizable carbon. The exact quantity of the carbon source which is used in the medium will depend, in part, upon the other ingredients in the medium, but is usually found in an amount ranging between 0.5 and 5 percent by weight. These carbon sources can be used individually in a given medium or several sources in combination in the same medium.

The preferred sources of nitrogen are amino acids such as glycine, methionine, proline, threonine and the like, as well as complex sources such as yeast extracts (hydrolysates, autolysates), dried yeast, tomato paste, soybean meal, peptone, corn steep liquor, distillers solubles, malt extracts and the like. Inorganic nitrogen sources such as ammonium salts (e.g. ammonium nitrate, ammonium sulfate, ammonium phosphate, etc.) can also be used. The various sources of nitrogen can be used alone or in combination in amounts ranging between 0.2 to 90 percent by weight of the medium.

The carbon and nitrogen sources are generally employed in combination, but need not be in pure form. Less pure materials which contain traces of growth factors, vitamins, and mineral nutrients may also be used. Mineral salts may also be added to the medium such as (but not limited to) calcium carbonate, sodium or potassium phosphate, sodium or potassium chloride, magnesium salts, copper salts, cobalt salts and the like. Also included are trace metals such as manganese, iron, molybdenum, zinc, and the like. In addition, if necessary, a defoaming agent such as polyethylene glycol or silicone may be added, especially if the culture medium foams seriously.

The preferred process for production of compounds of this invention consists of inoculating spores or mycelia of the producing organism into a suitable medium and then cultivating under aerobic condition.

The fermentation procedure generally is to first inoculate a preserved source of culture into a nutrient seed medium and to obtain, sometimes through a two step process, growth of the organisms which serve as seeds in the production of the active compounds. After inoculation, the flasks are incubated with agitation at temperatures ranging from 20° to 30° C., preferably 25° to 28° C. Agitation rates may range up to 400 rpm, preferably 200 to 220 rpm. Seed flasks are incubated over a period of 2 to 10 days, preferably 2 to 4 days. When growth is plentiful, usually 2 to 4 days, the culture may be used to inoculate production medium flasks. A second stage seed growth may be employed, particularly when going into larger vessels. When this is done, a portion of the culture growth is used to inoculate a second seed flask incubated under similar conditions but employing shorter time.

After inoculation, the fermentation production medium is incubated for 3 to 30 days, preferably 4 to 14 days, with or without agitation (depending on whether liquid or solid fermentation media are employed). The fermentation is conducted aerobically at temperatures ranging from 20° to 40° C. If used, agitation may be at a rate of 200 to 400 rpm. To obtain optimum results, the temperatures are in the range of 22° to 28° C., most preferably 24° to 26° C. The pH of the nutrient medium suitable for producing the active compounds is in the range of 3.5 to 8.5, most preferably 5.0 to 7.5. After the appropriate period for production of the desired compound, fermentation flasks are harvested and the active compound isolated.

An alcoholic solvent is employed to extract a compound of this invention from the solid fermentation medium. The preferred solvent for extraction of the solid fermentation is methanol. The mixture of alcoholic solvent and fermentation broth is vigorously stirred and filtered, and water added to the filtrate. The aqueous methanol extract is then adsorbed on an anion exchange resin. The preferred resin is Dowex-1 (Cl−). The active compound can be eluted from Dowex-1 using a high salt eluant; the preferred eluant is 3% ammonium chloride in 90% methanol/water. After elution from the ion exchange resin, the active compound may be recovered from the eluate by diluting the eluate with water, lowering the pH to 2.5, and extracting into an organic solvent; the preferred solvent for extraction is dichloromethane. The organic extract is then evaporated to afford partially purified active compound.

The active compound is further purified by chromatographic separation which may be carried out by employing reverse phase chromatagraphy. The preferred adsorbent for this chromatography is a C8 bonded phase silica gel. The preferred eluant for reverse phase chromatography is a mixture of acetonitrile and water buffered at a low pH, such as 0.1% phosphoric acid, or trifluoroacetic acid.

The present invention is also directed to a method of inhibiting cholesterol biosynthesis which comprises the administration to a subject in need of such treatment a nontoxic therapeutically effective amount of a compound represented by structural formula (I) and pharmaceutically acceptable salts thereof. Specifically, the compounds of this invention are useful as antihypercholesterolemic agents for the treatment of arteriosclerosis, hyperlipidemia, familial hypercholesterolemia and the like diseases in humans. They may be administered orally or parenterally in the form of a capsule, a tablet, an injectable preparation or the like. It is usually desirable to use the oral route. Doses may be varied, depending on the age, severity, body weight and other conditions of human patients, but daily dosage for adults is within a range of from about 20 mg to 2000 mg (preferably 20 to 100 mg) which may be given in two to four divided doses. Higher doses may be favorably employed as required.

The pharmaceutically acceptable salts of the compounds of this invention include those formed from cations such as sodium, potassium, aluminum, calcium, lithium, magnesium, zinc, and from bases such as ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. The salts included herein encompass those wherein one, two or all three of the carboxyl groups are in the salt form.

The compounds of this invention may also be coadministered with pharmaceutically acceptable nontoxic cationic polymers capable of binding bile acids in a non-reabsorbable form in the gastrointestinal tract. Examples of such polymers include cholestyramine, colestipol and poly[methyl-(3-trimethylaminopropyl)iminotrimethylene dihalide]. The relative amounts of the compounds of this invention and these polymers is between 1:100 and 1:15,000.

The intrinsic squalene synthetase inhibitory activity of representative compounds of this invention was measured by the standard in vitro protocol described below:

Preparation of Microsomes

Male, Charles River CD rats (120 to 150 g) were fed a diet containing 0.1% lovastatin for 4 days. The livers from these rats were homogenized in 5 volumes (ml/g) of ice cold 50 mM HEPES (4-(2-hydroxyethyl)-1-piperazine-ethanesulfonic acid), 5 mM EDTA(ethylenediaminetetraacetic acid) pH 7.5 with a Potter-Elvehjem type tissue grinder. The homogenate was centrifuged twice at 20,000 ×g for 15 minutes at 4° C., discarding the pellet each time. The supernatant was then centrifuged at 100,000×g for 1 hour at 4° C. The resulting microsomal pellet was resuspended in a volume of the above homogenizing buffer equal to one-fifth the volume of the original homogenate. This microsomal preparation has a protein concentration of about 7 mg/ml. The microsomal suspensions were stored in aliquots at −70° C. Squalene synthetase activity in these aliquots is stable for at least several months.

Partial Purification of Prenyl Transferase

Prenyl transferase was purified to use in the enzymatic synthesis of radiolabelled farnesyl pyrophosphate. Prenyl transferase was assayed by the method of Rilling (Methods in Enzymology 110, 125–129 (1985)) and a unit of activity is defined as the amount of enzyme that will produce 1μ mole of farnesyl pyrophosphate per minute at 30° C. in the standard assay.

The livers of 23 forty-day old male rats that had been fed 5% cholestyramine plus 0.1% lovastatin were homogenized in a Waring blender in 1 liter of 10 mM mercaptoethanol, 2 mM EDTA, 25 μM leupeptin, 0.005% phenylmethyl sulfonyl fluoride pH 7.0 containing 0.1 trypsin inhibitor units of aprotinin/ml. The homogenate was centrifuged at 20,000×g for 20 minutes. The supernatant was adjusted to pH 5.5. with 6N HOAc and centrifuged at 100,000×g for 1 hour. This supernatant was adjusted to pH 7.0 with 3N KOH and a 35–60% ammonium sulfate fraction taken. The 60% pellet was redissolved in 60 ml of 10 mM potassium phosphate, 10 mM mercaptoethanol, 1 mM EDTA pH 7.0 (Buffer A) and dialyzed against two 1 liter changes of Buffer A. This dialyzed fraction was applied to a 12.5×5 cm column of DEAE-sepharose 4B equilibrated with Buffer A. The column was washed with 700 ml of Buffer A and a 1 liter gradient from Buffer A to 100 mM potassium phosphate, 10 mM mercaptoethanol, 1 mM EDTA pH 7.0. Fractions having a specific activity greater than 0.20 units/mg were combined, solid ammonium sulfate was added to bring to 60% saturation and pelleted. The pellet was dissolved in 8 ml of 10 mM Tris, 10 mM β-mercaptoethanol pH 7.0 (Buffer B). The redissolved pellet was taken to 60% saturation with ammonium sulfate by adding 1.5 volumes of saturated ammonium sulfate in Buffer B. This ammonium sulfate suspension contained 3.5 units/ml with a specific activity of 0.23 units/mg and was free of isopentenyl pyrophosphate isomerase activity. This ammonium sulfate suspension was used for the synthesis of [4-$^{14}$C]farnesyl-pyrophosphate and its activity was stable stored at 4° C. for at least 6 months.

Enzymatic Synthesis of [4-$^{14}$C]farnesyl-pyrophosphate

The solvent (ethanol: 0.15N NH$_4$OH, 1:1) was removed from 55 μCi of [4-$^{14}$C]isopentenyl pyrophosphate (47.9 μCi/μmole) by rotary evaporation. Six hundred microliters of 100 mM Tris, 10 mM MgCl$_2$, 4 mM dithiothreitol pH 7.5 was added and the solution was transferred to a 1.5 ml Eppendorf centrifuge tube. Geranyl-pyrophosphate, 250 μl of a 20 mM solution, and 50 μl of the ammonium sulfate suspension of prenyl transferase were added to initiate the reaction. This incubation contained 5 μmoles of geranyl pyrophosphate, 1.15 μmoles of isopentenyl pyrophosphate, 6 μmoles of MgCl$_2$ of 0.18 units of prenyl transferase in a volume of 900 μl. The incubation was conducted at 37° C. During the incubation, the mix turned cloudy white as the newly formed magnesium complex of farnesyl pyrophoshate precipitated out of solution. The [4-$^{14}$C]farnesyl pyrophosphate was collected by centrifugation for 3 minutes at 14,000 rpm in an Eppendorf centrifuge tube, the supernatant removed, and the pellet was dissolved in 1.0 ml of 50 mM HEPES, 5 mM EDTA, pH 7.5 The yield was 50.7 μCi (92%) of [4-$^{14}$C]farnesyl pyrophosphate. The [4-$^{14}$C]farnesyl pyrophosphate was stored in aliquots at −70° C.

Squalene Synthetase Assay

Reactions were performed in 16×125 mm screw cap test tubes. A batch assay mix was prepared from the following solution:

| | μl per assay | volume for 50 assays |
|---|---|---|
| 1. 250 mM Hepes pH 7.5 | 20 | 1000 |
| 2. NaF 110 mM | 10 | 500 |
| 3. MgCl$_2$ 55 mM | 10 | 500 |
| 4. Dithiothreitol 30 mM | 10 | 500 |
| 5. NADPH 10 mM (made fresh) | 10 | 500 |
| 6. [4-$^{14}$C]farnesyl-pyrophosphate 47.9 μCi/μmole, and 0.025 μCi/3.0 μl | 3.0 | 150 |
| 7. H$_2$O | 24 | 1200 |

This assay mix was degassed under a vacuum and flushed with N$_2$. Solutions of the squalene synthetase inhibitors were prepared either in DMSO or MeOH and a 1:120 dilution of the microsomal protein was made with the original homogenizing buffer. For each reaction, 87 μl of the assay mix was taken with 3 μl of an inhibitor solution (DMSO or MeOH in the controls), warmed to 30° C. in a water bath and then the reaction was initiated by the addition of 10 μl of the 1:120 dilution of microsomal protein (0.6 μg protein total in the assay). The reactions were stopped after 20 minutes by the addition of 100 μl of a 1:1 mix of 40% KOH with 95% EtOH. The stopped mix was heated at 65° C. for 30 minutes, cooled, 10 ml of heptane was added and the mix was vortexed. Two g of activated alumina was then added, the mix vortexed again, the alumina allowed to settle and 5 ml of the heptane layer was removed. Ten ml of scintillation fluid was added to the heptane solution and radioactivity was determined by liquid scintillation counting.

Percent inhibition is caluated by the formula:

$$\left[1 - \frac{[\text{Sample} - \text{Blank}]}{[\text{Control} - \text{Blank}]}\right] \times 100$$

IC$_{50}$ values were determined by plotting the log of the concentration of the test compound versus the percentage inhibition. The IC$_{50}$ is the concentration of inhibitor that gives 50% inhibition as determined from these plots.

Representative of the intrinsic squalene synthetase inhibitory activities of the compounds of this invention is the IC$_{50}$ data tabulated below:

| Compound | Squalene Synthetase IC$_{50}$ |
|---|---|
| Compound A | 9 nM |

The present compounds also demonstrate broad spectrum antifungal activity as determined by broth and agar dilution methods. The compounds are particularly active towards filamentous fungi and yeasts including *Candida albicans* and *Cryptococcus neoformans*. The sensitivity of filamentous fungi and yeast was determined using inhibitor dilution assays in microtiter format. The compounds were dissolved in DMSO at 2 mg/ml and serially diluted in 0.1M phosphate buffer, pH 7.0 in the microtiter dish from 100 to 0.006 μg/ml. A standardized spore suspension for testing the filamentous fungi was prepared by inoculating Antibiotic Medium #3 containing 1.5% agar with spores such that 1.5×10$^3$ colony forming units were added per well. The microtiter wells were filled with 50 μl of buffer containing compound and 50 μl of inoculated medium.

The sensitivity of yeasts was determined by inoculating yeast nitrogen base containing 1% dextrose (YNB/G) with aliquots of an overnight yeast culture grown in Yeast Morphology (YM) media at 35° C. and diluting in YNB/G to yield a final concentration of 1.5-7.5×10$^3$ colony forming units/well. To test the sensitivity of yeast, compound was solubilized in 10 percent aqueous DMSO at 2.56 mg/ml. The compound was diluted serially in YNB/G from 128 to 0.06 μg/ml and further diluted 1:10 in YNB/G. The wells were filled with 150 μl of media containing drug. The minimum inhibitory concentration (MIC) is defined as the lowest concentration to prevent growth after an incubation for 42 hours, at 28° C. for the filamentous fungi and 24 to 48 hours, at 35° C. for the yeasts. Representative of the antifungal activity are the minimum inhibitory concentration data shown below.

Minimum Inhibitory Concentration (mcg/ml)

| Organism | Compound A |
| --- | --- |
| Filamentous Fungi | |
| *Aspergillus flavus* MF383 | 1.5 |
| *A. nidulans* R21 | 1.5 |
| Yeast | |
| *Candida albicans* MY1055 | 16 |
| *C. tropicalis* MY1012 | 8 |
| *C. parapsilosis* MY1010 | 8 |
| *Crypt. neoformans* MY1051 | 1 |

Thus the present invention is also directed to a method of treating fungus infections which comprises the administration to an organism in need of such treatment a nontoxic therapeutically effective amount of a compound represented by the structural formula (I) and pharmaceutically acceptable salts thereof. Based on the above MIC data it is determined that generally from 2 to about 20 mg/kg should be employed as a unit dosage in an antifungal treatment.

The compounds of this invention are adaptable to being utilized in various applications of antifungal compositions. In such use, compounds may be admixed with a biologically inert carrier, generally with the aid of a surface active dispersing agent, the nature of which would vary depending on whether the use is for the control of pathogens infecting mammals such as man, or birds or reptiles, or for control of fungi in agriculture such as in soil or plant parts, or for the control of fungi in inanimate objects.

In compositions for medical applications, the compounds may be admixed with a pharmaceutically acceptable carrier, the nature of which will vary depending on whether the composition is to be topical, parenteral or oral.

If said application is to be topical, the drug may be formulated in conventional creams and ointments such as white petroleum, anhydrous lanolin, cetyl alcohol, cold cream, glyceryl monostearate, rose water and the like.

For parenteral applications, the compounds may be formulated in conventional parenteral solutions such as 0.85 percent sodium chloride or 5 percent dextrose in water, or other pharmaceutically acceptable compositions.

Compositions for oral administration may be prepared by intimately mixing the component drugs with any of the usual pharmaceutical media, including, for liquid preparations, liquid carriers such as water, glycols, oils, alcohols, and the like; and for solid preparations such as capsules and tablets, solid carriers such as starches, sugars, kaolin, ethyl cellulose, surface active dispersing agents, generally with lubricant such as calcium stearate, together with binders, disintegrating agents and the like.

These compositions are then administered in amounts sufficient to obtain the desired antifungal effect. For medical application, the method comprises administering to a subject in need of treatment a therapeutically effective antifungal amount of a compound of Formula I. The appropriate doses will vary depending on age, severity, body weight and other conditions. For topical application the compositions are applied directly to the area where control is desired. For internal administration, the composition may be applied by injection or may be administered orally.

For non-medical application, the product of the present invention, either singly or as a mixture, may be employed in compositions in an inert-carrier which includes finely divided dry or liquid diluents, extenders, fillers, conditioners and excipients, including various clays, diatomaceous earth, talc, and the like, or water and various organic liquids such a lower alkanols, for example ethanol and isopropanol, or kerosene, benzene, toluene and other petroleum distillate fractions or mixtures thereof.

These compositions may be employed by applying to the surface of or incorporating in the medium to be protected. For the control of rice blast, tomato late blight, tomato early blight, wheat leaf rust, bean powdery mildew and tomato Fusarium wilt, the compositions may be applied directly to the plant in topical application or administered to the soil for systemic application. The method comprises administering to the affected plant, soil or medium to be protected an antifungally effective amount of the compound of Formula I.

The following examples illustrate the preparation of the compounds of formula (I) and their incorporation into pharmaceutical compositions and, as such, are not to be considered as limiting the invention set forth in the claims appended hereto.

The composition of media employed in the following Examples are listed below:

| KF SEED MEDIUM | per liter | Trace Element Mix #2 | g/L |
| --- | --- | --- | --- |
| Corn Steep Liquor | 5 g | $FeSO_4.7H_2O$ | 1.0 |
| Tomato Paste | 40 g | $MnSO_4.4H_2O$ | 1.0 |
| Oat Flour | 10 g | $CuCl_2.2H_2O$ | 0.025 |
| Cerelose | 10 g | $CaCl_2.2H_2O$ | 0.1 |
| Trace Element Mix #2 | 10 ml | $(NH_4)_6Mo_7O_{24}.4H_2O$ | 0.019 |
| Distilled Water | 1000 ml | $ZnSO_4.7H_2O$ | 0.2 |
| pH adjusted to 6.8 (presterile) | | | |
| 50 mls/nonbaffled 250 mls Erlenmeyer flask autoclave 20 minutes (121° C., 15 psi) | | dissolved in 1 L 0.6 N HCl | |

Production Media

| F1 | | BRF | |
| --- | --- | --- | --- |
| Cracked corn | 10.0 g/flask | Brown rice | 5.0 g/flask |
| Base liquid #3 | 10.0 mls/flask | Base liquid #2 | 20.0 mls/flask |

| Base liquid #3 | g/L | Base liquid #2 | g/L |
| --- | --- | --- | --- |
| Ardamine PH | 0.2 | Yeast extract | 1.0 |
| $KH_2PO_4$ | 0.1 | Sodium tartrate | 0.5 |
| $MgSO_4.7H_2O$ | 0.1 | $KH_2PO_4$ | 0.5 |
| Sodium tartrate | 0.1 | distilled water | 1000.0 mls |
| $FeSO_4.7H_2O$ | 0.01 | | |
| $ZnSO_4.7H_2O$ | 0.01 | (no pH adjustment) | |
| distilled $H_2O$ | 1000.0 mls | | |
| (no pH adjustment) | | autoclave 15 minutes (121° C., 15 psi) add 15.0 mls distilled $H_2O$/flask | |
| autoclave 15 minutes (121° C., 15 psi) add 15.0 mls distilled $H_2O$/flask autoclave 20 minutes (121° C., 15 psi) | | autoclave 20 minutes (121° C., 15 psi) | |

EXAMPLE 1

Preparation of Compound A

A. Culturing MF5465

Culture MF5465, inoculated from a soil tube using one glass scoop of soil, was grown in 3 KF seed medium flasks for 74 hours at 25° C., 220 rpm, 85% humidity. The flasks were then pooled, and sterile glycerol added to obtain a final concentration of 10%. The contents were mixed and 2.0 ml aliquots were dispensed aseptically into sterile cryotubes. The vials were frozen and maintained at $-80°$ C.

Three vails containing frozen vegetative mycelia were defrosted and transfered, one to each of three KF seed medium flasks. These seed flasks were incubated for 71 hours at 25° C., 220 rpm, 85% humidity. At completion of the incubation, the three KF flasks were pooled and the seed was used to inoculate 56 F1 production medium flasks. Care was taken to manually distribute seed growth throughout the solid production medium. Production flasks were incubated statically at 25° C. for 21 days. Flasks were harvested as follows: 45 mls 75% methanol was added to each production flask; growth was manually broken apart into small fragments by use of a glass pipette; flasks were re-stoppered and placed onto a gyrotory shaker and agitated for 30 minutes at 220 rpm while the extraction proceeded. After shaking, the contents of the individual flasks were pooled by pouring the solvent-extract off the mycelial covered corn and into a 2 liter Erlenmeyer flask. Contents of each flask were then subjected to a second extraction with another 45 mls 75% methanol. Extraction proceeded as above with the resultant extracts being pooled into a second 2 liter Erlenmeyer flask.

B. Isolation of Compound A

The extracts from above (4800 mL) were loaded onto a DOWEX-1 column (500 mL resin) at a rate of 20 mL/min. The column was then washed with 50% methanol/water (300 mL), and 90% methanol/water (500 mL), and then eluted with 3% ammonium chloride in 90% methanol/water. Six fractions (500 mL) were collected. The first 3 fractions were combined, diluted with water (1 L), and adjusted to pH 2.5 with conc. hydrochloric acid. The acidified eluate was extracted with dichloromethane ($2 \times 500$ mL). Evaporation of the dichloromethane extract afforded an oily residue (402 mg). The residue was dissolved in methanol (1.2 ml) and loaded on a prep HPLC column (Dynamax 60A, 8 um C8, $24.6 \times 250$ mm with guard column). The column was eluted with 72% acetonitrile/28% (0.1% phosphoric acid in water) with a 10 mL/min flow rate. Collecting 5 mL fractions, the desired compound eluted in fractions 29–34. Fractions 29–34 were combined and ethyl acetate (30 mL) was added. After washing with water (10 mL), the organic layer was evaporated to give Compound A as an oil.

EXAMPLE 2

Preparation of an Ammonium Salt

A 0.1 mmol sample of the free acid of a compound of formula (I) is dissolved in 10 ml of ethyl acetate. The resulting solution is saturated with gaseous ammonia upon which the ammonium salt precipitates from solution.

EXAMPLE 3

Preparation of a Potassium Salt

A solution of 0.1 mmol of the free acid of a compound of formula (I) in 10 ml of methanol is treated with an aqueous or methanolic solution containing 0.3 mmol of potassium hydroxide. Evaporation of the solvent affords the tri-potassium salt. Addition of between 0.1 and 0.3 mmol of potassium hydroxide yields analogously mixtures of the mono-potassium, di-potassium and tri-potassium salts whose composition depends upon the exact amount of potassium hydroxide added.

In a similar fashion the sodium and lithium salts can be formed.

EXAMPLE 4

Preparation of a Calcium Salt

A solution of 0.1 mmol of the free acid of a compound of formula (I) in 20 ml of 6:4 methanol/water is treated with an aqueous solution of 0.1 mmol of calcium hydroxide. The solvents are evaporated to give the corresponding calcium salt.

EXAMPLE 5

Preparation of an Ethylenediamine Salt

A solution of 0.1 mmol of the free acid of a compound of formula (I) in 10 ml of methanol is treated with 0.1 mmol of ethylenediamine. Evaporation of the solvent affords the ethylenediamine salt.

The procedure can also be applied to the preparation of the N,N"-dibenzylethylenediamine salt.

EXAMPLE 6

Preparation of a Tris(hydroxymethyl)aminomethane Salt

To a solution of 0.1 mmol of the free acid of a compound of formula (I) in 10 ml of methanol is added from 0.1 to 0.3 mmol of tris(hydroxymethyl)aminomethane dissolved in 10 ml of methanol. Evaporation of the solvent gives a corresponding salt form, the exact composition of which is determined by the molar ratio of amine added. Similarly prepared are the salts of L-ornithine, L-lysine, and N-methylgluacamine.

EXAMPLE 7

Preparation of an L-arginine Salt

A solution of 0.1 mmol of the free acid of a compound of formula (I) in 20 ml of 6:4 methanol/water is treated with an aqueous solution of 0.1 to 0.3 mmol of L-arginine. Evaporation of the solvent affords the title salt, the exact composition of which is determined by the molar ratio of amino acid to the free acid of formula (I) used.

Similarly prepared are the salts of L-ornithine, L-lysine and N-methylglucamine.

EXAMPLE 8

Preparation of a Compound B (Method 1)

To 5 mg of L-697,350 in methanol (5 ml) was added 2 ml of freshly distilled diazomethane in ether (2.05M). After 5 minutes the solvent was removed to afford trimethyl ester (Compound B) as an oil.

EXAMPLE 9

Preparation of Compound B (Method 2)

A solution of 2 mg of Compound A in 0.5 ml of acetonitrile is treated at room temperature with 10 equivalents of DBU and 10 equivalents of MeI. After 2 hours the reaction is diluted with 10 ml of dichloromethane and washed successively with 10 ml of 0.1M phosphoric acid, 10 ml of water, 10 ml of saturated sodium bicarbonate and 10 ml of water. After drying over sodium sulfate, the organic layer is concentrated and the residue is chromatographed on silica gel using mixtures of hexane and ethyl acetate to give Compound B.

The method of Example 9 is also suitable for the preparation of other ester derivatives such as 1) ethyl and other lower alkyl esters and 2) benzyl and substituted benzyl esters.

Mass Spectral Data

Mass spectra were recorded on Finnigan-MAT model MAT212 (electron impact, EI, 90 eV), MAT 90 (Fast Atom Bombardment, FAB), and TSQ70B (FAB, EI) mass spectrometers. Exact mass measurements were performed at high resolution (HR-EI) using perfluorokerosene (PFK) or perfluoropolypropylene oxide (Ultramark U1600F) as internal standard. Trimethylsilyl derivatives were prepared with a 1:1 mixture of BSTFA-pyridine at room temperature.

$^{13}C$ NMR Data $^{13}C$ NMR spectra were recorded in $CD_3OD$ at 75 MHz on a Varian XL-300 spectrometer. Chemical shifts are given in ppm relative to TMS at zero ppm using the solvent peak at 49.0 ppm ($CD_3OD$) as internal standard.

$^1H$ NMR Spectra $^1H$ NMR spectra were recorded at 300 MHz on a Varian XL-300 spectrometer. Chemical shifts are shown in ppm relative to TMS at zero ppm using the solvent peaks at 3.30 ppm ($CD_3OD$) as internal standards.

Physical Properties of the compounds of Structure I

Compound A-the compound of structure (I) wherein $Z_1$ $Z_2$ and $Z_3$ are each hydrogen.

Mass Spectral Data

This compound has the molecular weight 754. The molecular formula $C_{40}H_{50}O_{14}$ was determined by HR-MS measurement of the penta-trimethylsilyl derivative (calc for $C_{40}H_{50}O_{14}$ 754.3198, found 754.3154.

$^1H$ NMR spectrum (300 MHz) ($CD_3OD$, 22° C.): 7.22 (m, 4H), 7.13 (m, 6H), 6.23 (d, 1.8), 5.36 (m, 2H), 5.24 (s), 4.88 (q, 3.9), 4.03 (d, 1.8), 2.73 (dd, 13.3, 5.6 Hz), 2.54 (t, 7.6, 2H), 2.3 (m, 5H), 2.04 (s, 3H), 2.04 (m, 2H), 1.89 (br t, 7.0, 2H), 1.6 (m, 5H), 1.27 (m, 2H), 0.93 (d, 6.8, 3H), 0.86 (d, 6.8, 3H), ppm.

$^{13}C$ NMR ($CD_3OD$): 173.06, 173.04, 172.43, 170.14, 168.46, 143.84, 141.88, 138.78, 130.15 (2×), 129.36 (2×), 129.24 (4×), 127.53, 126.89, 126.61, 107.17, 90.94, 82.15, 81.11, 78.10, 76.57, 75.56, 40.46, 39.62, 37.77, 37.56, 36.87, 36.21, 35.34, 32.43, 30.44, 28.75, 21.25, 21.13, 20.08, 14.32 ppm.

IR (as a free acid; film on ZnSe): 3200 br, 2936, 1733, 1496, 1454, 1437, 1375, 1250, 1180, 1148, 1026, 972, 898, 831, 746, 700 cm$^{-1}$.

Compound B-the trimethyl ester of Compound A, i.e. the compound of structure (I) wherein $Z_1$, $Z_2$ and $Z_3$ are each methyl.

Mass Spectral Data

This compound has the molecular weight 796 by FAB-MS (observed $[M+Cs]^{30}$ at m/z 929.

$^1H$ NMR Spectrum (300 MHz) ($CD_3OD_6$, 22° C.): 7.22 (m, 6H), 7.15 (m, 4H), 6.16 (d, 1.9), 5.32 (m, 2H), 5.24 (s), 4.9 (m), 4.00 (d, 1.9), 3.81 (s, 3H), 3.70 (s, 3H), 3.68 (s, 3H), 2.73 (dd, 13.3, 5.7 Hz), 2.56 (dt, 2.5, 7.6, 2H), 2.35 (m, 3H), 2.25 (m, 2H), 2.08 (m), 2.05 (s, 3H), 2.01 (m), 1.88 (br t, 7.4, 2H), 1.68 (m, 2H), 1.56 (m, 3H), 1.29 (m, 2H), 0.94 (d, 6.8, 3H), 0.86 (d, 6.8, 3H) ppm.

$^{13}C$ NMR Chemical Shifts $^{13}C$ NMR ($CD_3OD$): 173.04, 172.85, 171.16, 168.75, 167.39, 143.94, 141.98, 138.96, 130.21 (2×), 129.43 (2×), 129.30 (4×), 127.49, 126.96, 126.66, 107.49, 91.12, 81.89, 81.17, 78.04, 76.83, 76.20, 53.62, 53.03, 52.77, 40.52, 39.75, 37.87, 37.61, 36.93, 36.09, 35.19, 32.46, 30.53, 28.78, 21.27, 21.13, 20.13, 14.35 ppm.

IR (film on ZnSe): 3200 br, 2917, 2848, 1738, 1603, 1441, 1371, 1246, 1149, 1124, 1030, 968, 748, 702 cm$^{-1}$.

What is claimed is:

1. A compound of structural formula (I)

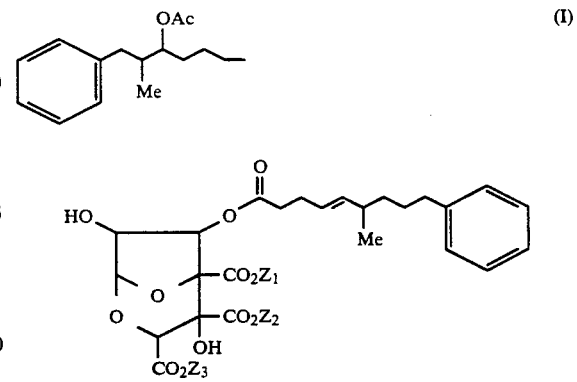

wherein $Z_1$ $Z_2$ and $Z_3$ are each independently selected from
 a) H;
 b) $C_{1-5}$ alkyl;
 c) $C_{1-5}$ alkyl substituted with a member of the group consisting of
  i) phenyl,
  ii) phenyl substituted with methyl, methoxy, halogen (Cl, Br, I, F) or hydroxy;

or a pharmaceutically acceptable salt of a compound of formula (I).

2. A compound of claim 1 wherein the stereochemical configuration of structural formula (I) is selected from the group consisting of:

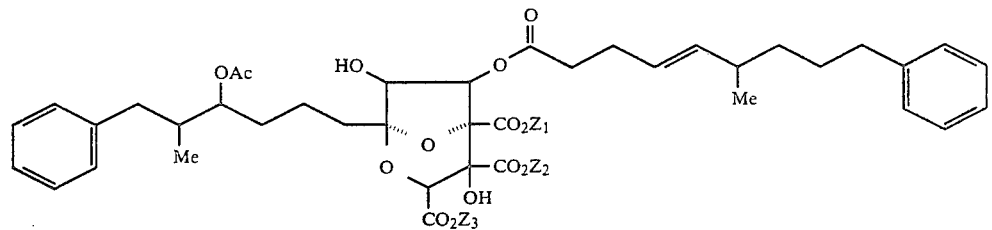
a)
and
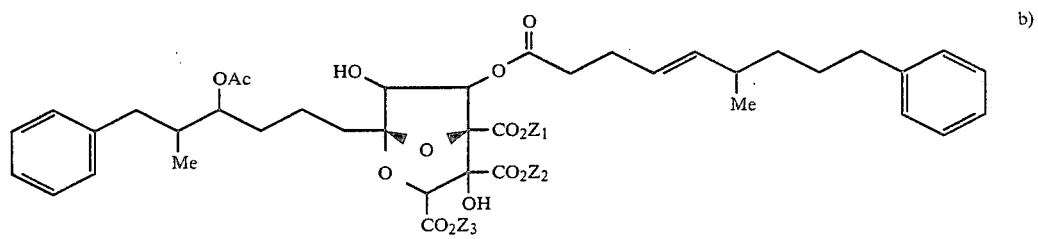
b)
3. A compound of claim 2 wherein the stereochemical configuration within structural formula (I) is selected from the group consisting of:
4. A compound of claim 3 wherein the stereochemical configuration of structural formula (I) is selected from the group consisting of:
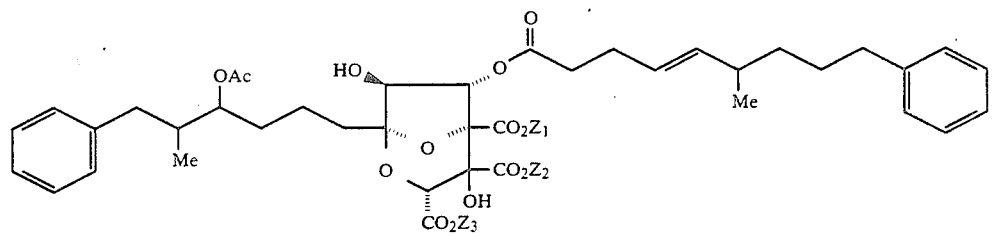
a)
and
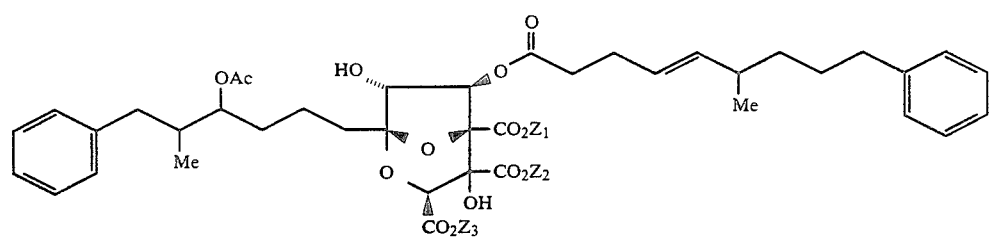
b)
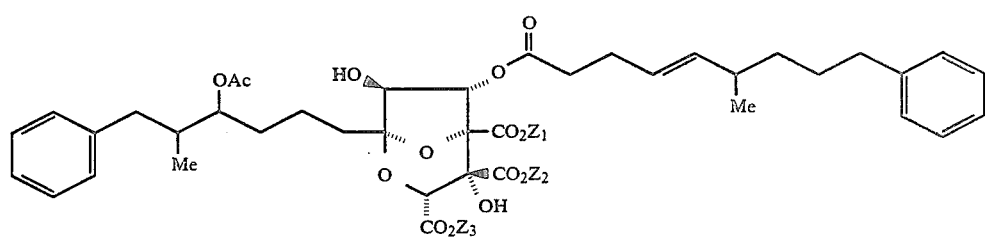
a)
and -continued

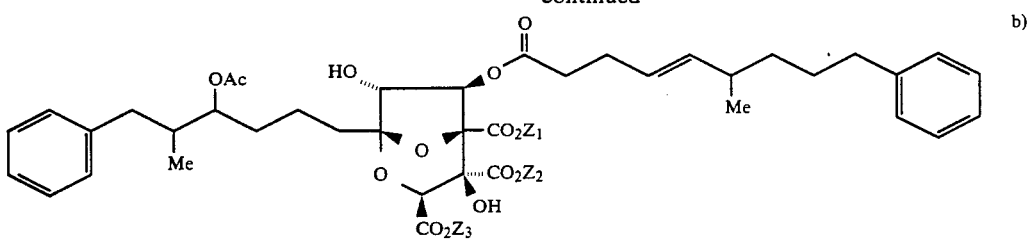
b)

5. A compound of claim 4 in which $Z_1$, $Z_2$ and $Z_3$ are each hydrogen or a pharmaceutically acceptable salt thereof.

6. A compound of claim 4 in which $Z_1$, $Z_2$ and $Z_3$ are each methyl.

7. A compound of claim 1 which is:

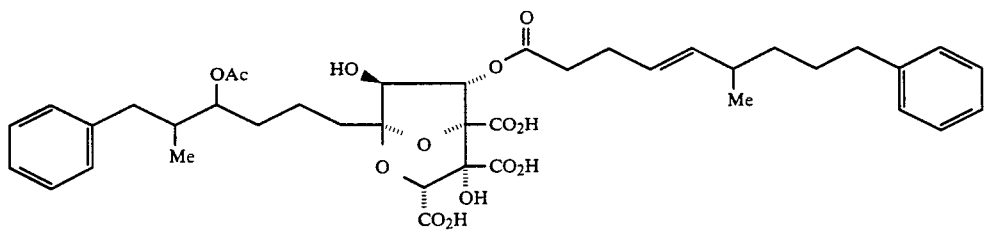

8. A compound of molecular formula $C_{40}H_{50}O_{14}$ and molecular weight 754 characterized by the (a) $^{13}C$ NMR chemical shifts, as measured in $CD_3OD$ at 22° C.: 173.06, 173.04, 172.43, 170.14, 168.46, 143.84, 141.88, 138.78, 130.15 (2×), 129.36 (2×), 129.24 (4×), 127.53, 126.89, 126.61, 107.17, 90.94, 82.15, 81.11, 78.10, 76.57, 75.56, 40.46, 39.62, 37.77, 37.56, 36.87, 36.21, 35.34, 32.43, 30.44, 28.75, 21.25, 21.13, 20.08, 14.32 ppm.

(b) $^1H$ NMR chemical shifts, as measured in $CD_3OD$ at 22° C.: 7.22 (m, 4H), 7.13 (m, 6H), 6.23 (d, 1.8), 5.36 (m, 2H), 5.24 (s), 4.88 (q, 3.9), 4.03 (d, 1.8), 2.73 (dd, 13.3, 5.6 Hz), 2.54 (t, 7.6, 2H), 2.3 (m, 5H), 2.04 (s, 3H), 2.04 (m, 2H), 1.89 (br t, 7.0, 2H), 1.6 (m, 5H), 1.27 (m, 2H), 0.93 (d, 6.8, 3H), 0.86 (d, 6.8, 3H), ppm.

9. A pharmaceutical composition comprising a nontoxic anti-cholesterolemically effective amount of a compound of claim 1 and a pharmaceutically acceptable carrier.

10. A composition of claim 9 wherein the therapeutically effective compound is selected from the group consisting of:

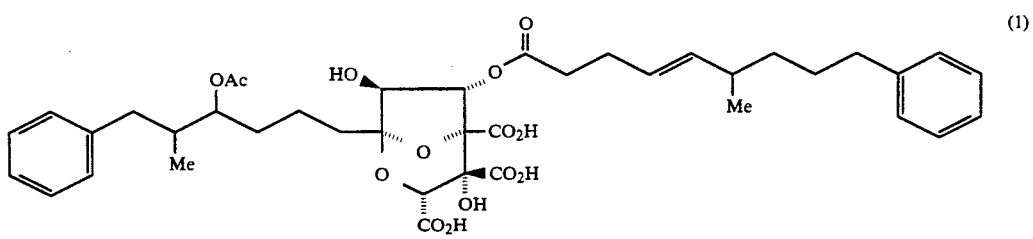
(1)

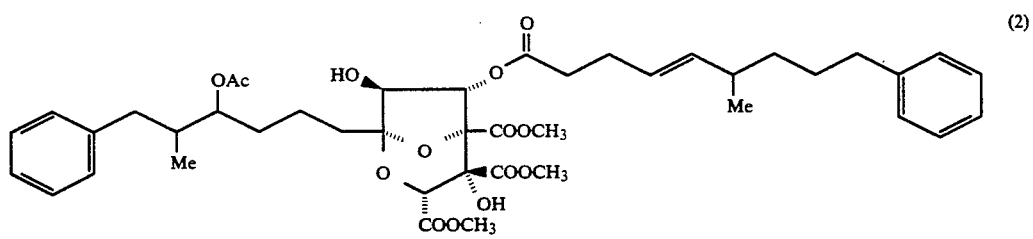
(2)

11. A method of treating hypercholesterolemia comprising the administration to a subject in need of such treatment a nontoxic therapeutically effective amount of a compound of claim 1.

12. A method of claim 11 wherein the therapeutically effective compound is selected from the group consisting of:

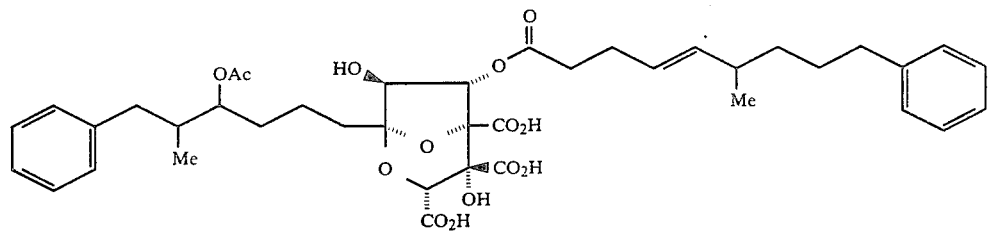
(1)
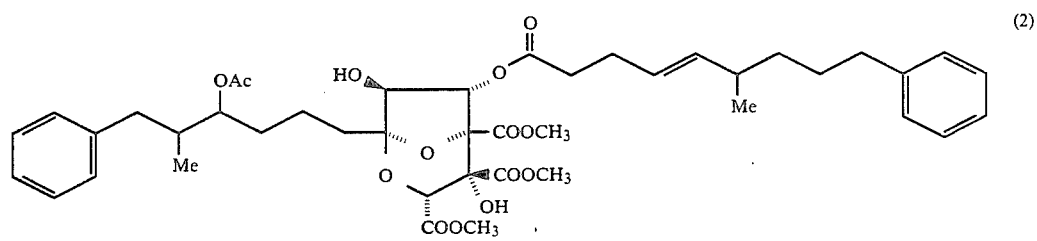
(2)